(12) United States Patent
Smith et al.

(10) Patent No.: US 11,795,108 B2
(45) Date of Patent: Oct. 24, 2023

(54) MICROORGANISM LOADED AGGREGATE AND MANUFACTURING METHODS

(71) Applicant: Biomason Inc., Research Triangle Park, NC (US)

(72) Inventors: Kent J. Smith, Durham, NC (US); Cameron Arnette, Raleigh, NC (US); Ginger K. Dosier, Raleigh, NC (US); John Michael Dosier, Raleigh, NC (US)

(73) Assignee: BIOMASON INC., Durham, NC (US)

( * ) Notice: Subject to any disclaimer, the term of this patent is extended or adjusted under 35 U.S.C. 154(b) by 770 days.

(21) Appl. No.: 15/795,931

(22) Filed: Oct. 27, 2017

(65) Prior Publication Data

US 2018/0118623 A1     May 3, 2018

Related U.S. Application Data

(60) Provisional application No. 62/414,876, filed on Oct. 31, 2016.

(51) Int. Cl.
| | |
|---|---|
| C04B 24/00 | (2006.01) |
| C04B 18/02 | (2006.01) |
| C09K 3/22 | (2006.01) |
| C12N 3/00 | (2006.01) |
| C12N 1/20 | (2006.01) |
| C12P 3/00 | (2006.01) |
| C04B 103/00 | (2006.01) |
| C04B 111/00 | (2006.01) |

(52) U.S. Cl.
CPC .............. *C04B 24/00* (2013.01); *C04B 18/02* (2013.01); *C04B 18/021* (2013.01); *C04B 18/022* (2013.01); *C09K 3/22* (2013.01); *C12N 1/20* (2013.01); *C12N 3/00* (2013.01); *C12P 3/00* (2013.01); *C12Y 305/01005* (2013.01); *C12Y 402/01001* (2013.01); *C04B 2103/0001* (2013.01); *C04B 2103/0075* (2013.01); *C04B 2111/00017* (2013.01); *Y02W 30/91* (2015.05)

(58) Field of Classification Search
None
See application file for complete search history.

(56) References Cited

U.S. PATENT DOCUMENTS

| | | | |
|---|---|---|---|
| 3,667,976 A | 6/1972 | Tanner et al. | |
| 3,829,553 A | 8/1974 | Lynn | |
| 4,204,876 A | 5/1980 | Bowden | |
| 4,617,326 A | 10/1986 | Bjornberg et al. | |
| 4,946,505 A | 8/1990 | Jungk | |
| 5,143,155 A | 9/1992 | Ferris et al. | |
| 5,199,986 A | 4/1993 | Krockert et al. | |
| 5,558,708 A | 9/1996 | Johansen, Jr. et al. | |
| 5,846,315 A | 12/1998 | Johansen, Jr. et al. | |
| 5,891,205 A | 4/1999 | Picardi et al. | |
| 6,348,147 B1 | 2/2002 | Long | |
| 7,025,824 B2 | 4/2006 | Axen et al. | |
| 7,101,430 B1 | 9/2006 | Pike et al. | |
| 8,182,604 B2 | 5/2012 | Kucharski et al. | |
| 8,420,362 B2 | 4/2013 | Crawford et al. | |
| 8,470,275 B2 | 6/2013 | Constantz et al. | |
| 8,518,177 B2 | 8/2013 | Chattopadhyay et al. | |
| 8,728,365 B2 | 5/2014 | Dosier | |
| 8,911,549 B2 | 12/2014 | Jonkers | |
| 8,912,244 B2 | 12/2014 | Vitomir et al. | |
| 8,932,400 B2 | 1/2015 | Chen et al. | |
| 8,951,786 B1 | 2/2015 | Dosier | |
| 9,074,134 B2 | 7/2015 | Bang et al. | |
| 9,199,880 B2 | 12/2015 | Dosier | |
| 9,428,418 B2 | 8/2016 | Dosier | |
| 9,796,626 B2 | 10/2017 | Dosier | |
| 10,125,303 B2 | 11/2018 | Wilson et al. | |
| 10,450,695 B2 | 10/2019 | Dosier et al. | |
| 10,626,547 B2 | 4/2020 | Dosier et al. | |
| 10,717,674 B2 | 7/2020 | Hill et al. | |
| 11,008,591 B2 | 5/2021 | Dosier et al. | |
| 11,472,738 B2 | 10/2022 | Hill et al. | |
| 2005/0029187 A1 | 2/2005 | Koga et al. | |
| 2005/0103204 A1 | 5/2005 | Halliday et al. | |
| 2005/0103234 A1 | 5/2005 | McNulty | |
| 2007/0216058 A1 | 9/2007 | Carreras-Maldonado et al. | |
| 2008/0245272 A1 | 10/2008 | Kucharski et al. | |
| 2010/0086367 A1 | 4/2010 | Darson-Baulleur | |
| 2010/0210745 A1 | 8/2010 | McDaniel et al. | |

(Continued)

FOREIGN PATENT DOCUMENTS

| | | |
|---|---|---|
| CA | 2591097 | 6/2006 |
| CN | 1101626 A | 4/1995 |

(Continued)

OTHER PUBLICATIONS

Supplemental Search Report for EPO Application No. 17864205.4 dated May 19, 2020.

(Continued)

*Primary Examiner* — Nghi V Nguyen
(74) *Attorney, Agent, or Firm* — Wilson Sonsini Goodrich & Rosati

(57) ABSTRACT

The invention is directed to compositions, tools and methods for the manufacture of construction materials, masonry, solid structures and compositions to facilitate dust control. More particularly, the invention is directed to the manufacture of bricks, masonry and other solid structures using small amount of aggregate material that is pre-loaded with spores and/or vegetative bacterial cells.

19 Claims, No Drawings

(56) References Cited

U.S. PATENT DOCUMENTS

| | | |
|---|---|---|
| 2011/0011303 A1 | 1/2011 | Jonkers |
| 2011/0027850 A1 | 2/2011 | Crawford et al. |
| 2011/0067600 A1 | 3/2011 | Constantz et al. |
| 2011/0262640 A1 | 10/2011 | Dosier |
| 2012/0199046 A1 | 8/2012 | Jonkers |
| 2013/0112114 A1 | 5/2013 | Jonkers |
| 2013/0196419 A1 | 8/2013 | Chavez Crooker |
| 2014/0239535 A1 | 8/2014 | Dosier |
| 2014/0248681 A1 | 9/2014 | Soens |
| 2014/0369749 A1 | 12/2014 | Friedman et al. |
| 2015/0264898 A1 | 9/2015 | Ortego et al. |
| 2015/0322604 A1 | 11/2015 | Brunner et al. |
| 2016/0010434 A1 | 1/2016 | Portman et al. |
| 2016/0068438 A1 | 3/2016 | Dosier |
| 2016/0090328 A1 | 3/2016 | Wiktor et al. |
| 2016/0130489 A1 | 5/2016 | Gilmour |
| 2016/0174530 A1 | 6/2016 | Barber |
| 2016/0264463 A1 * | 9/2016 | Dosier .................. C12N 11/02 |
| 2016/0362334 A1 | 12/2016 | Dosier |
| 2017/0015832 A1 * | 1/2017 | Berlin .................. C09C 1/3676 |
| 2017/0190617 A1 | 7/2017 | Hill |
| 2017/0190620 A1 * | 7/2017 | Jonkers .................. C12N 1/20 |
| 2018/0118623 A1 | 5/2018 | Smith |
| 2018/0244585 A1 | 8/2018 | Rahbar et al. |
| 2018/0305858 A1 | 10/2018 | Dosier et al. |
| 2019/0106716 A1 | 4/2019 | Dosier et al. |
| 2019/0106717 A1 | 4/2019 | Dosier et al. |
| 2019/0210924 A1 | 7/2019 | Royne et al. |
| 2020/0171533 A1 | 6/2020 | Dosier et al. |
| 2020/0262711 A1 | 8/2020 | Dosier et al. |
| 2020/0331804 A1 | 10/2020 | Hill et al. |
| 2020/0346976 A1 | 11/2020 | Hill et al. |
| 2021/0189238 A1 | 6/2021 | Kavazanjian et al. |
| 2022/0126317 A1 | 4/2022 | Dosier et al. |

FOREIGN PATENT DOCUMENTS

| | | | |
|---|---|---|---|
| CN | 1125472 A | 6/1996 | |
| CN | 1285401 A | 2/2001 | |
| CN | 1778934 A | 5/2006 | |
| CN | 1807358 | 7/2006 | |
| CN | 101270369 A2 | 9/2008 | |
| CN | 101054568 B | 5/2010 | |
| CN | 102121033 A | 7/2011 | |
| CN | 102587875 A | 7/2012 | |
| CN | 103173376 A | 6/2013 | |
| CN | 103173376 B | 10/2014 | |
| CN | 104071890 A | 10/2014 | |
| CN | 105080932 A | 11/2015 | |
| CN | 105418013 A | 3/2016 | |
| CN | 105837075 A | 8/2016 | |
| CN | 105884308 A | 8/2016 | |
| CN | 105924053 A | 9/2016 | |
| CN | 105925512 A | 9/2016 | |
| CN | 108956667 A | 12/2018 | |
| EP | 0388304 | 9/1990 | |
| EP | 0631998 | 1/1995 | |
| EP | 1838642 | 10/2007 | |
| EP | 1893546 | 3/2008 | |
| EP | 2082999 A1 * | 7/2009 | ......... C04B 20/1022 |
| EP | 2082999 A1 | 7/2009 | |
| EP | 2247551 | 11/2010 | |
| EP | 2297062 | 3/2011 | |
| EP | 2429970 | 3/2012 | |
| EP | 2462232 | 6/2012 | |
| EP | 2940122 A1 | 11/2015 | |
| JP | S63227330 A | 9/1988 | |
| JP | H05253908 A | 10/1993 | |
| JP | 2006144285 A | 6/2006 | |
| JP | 2007284974 A | 11/2007 | |
| JP | 2008524096 A | 7/2008 | |
| JP | 2009270302 A | 11/2009 | |
| JP | 2011509915 A | 3/2011 | |
| JP | 2012019751 A | 2/2012 | |
| JP | 2013523590 A | 6/2013 | |
| JP | 5253908 B2 | 7/2013 | |
| JP | 5284646 | 9/2013 | |
| JP | 2014510689 A | 5/2014 | |
| WO | WO-0248069 A1 | 6/2002 | |
| WO | WO-03055450 A1 | 7/2003 | |
| WO | WO2006/066326 A1 | 6/2006 | |
| WO | WO-2007044439 A2 | 4/2007 | |
| WO | WO2007/070706 A2 | 6/2007 | |
| WO | WO-2008009771 A1 | 1/2008 | |
| WO | WO2008120979 | 10/2008 | |
| WO | WO-2009009838 A1 | 1/2009 | |
| WO | WO-2009093898 A1 | 7/2009 | |
| WO | WO2010/130712 A1 | 11/2010 | |
| WO | WO2011126361 | 10/2011 | |
| WO | WO-2011137106 A1 | 11/2011 | |
| WO | WO-2012113765 A1 | 8/2012 | |
| WO | WO-2013120847 A1 | 8/2013 | |
| WO | WO2014185781 | 11/2014 | |
| WO | WO2015042031 | 3/2015 | |
| WO | WO2015155769 | 10/2015 | |
| WO | WO2016010434 | 1/2016 | |
| WO | WO-2016010434 A1 * | 1/2016 | ........... C04B 18/141 |
| WO | WO-2016144786 A1 | 9/2016 | |
| WO | WO-2016145190 A1 | 9/2016 | |
| WO | WO-2017139750 A1 | 8/2017 | |
| WO | WO-2017189106 A1 | 11/2017 | |
| WO | WO-2017220768 A1 | 12/2017 | |
| WO | WO 2018/064320 | 4/2018 | |
| WO | WO-2018081542 A1 | 5/2018 | |
| WO | WO-2018200684 A1 | 11/2018 | |
| WO | WO-2019071172 A1 | 4/2019 | |
| WO | WO-2019071175 A1 | 4/2019 | |
| WO | WO-2020168342 A1 | 8/2020 | |
| WO | WO-2020180914 A1 | 9/2020 | |
| WO | WO-2020198295 A1 | 10/2020 | |
| WO | WO-2022010915 A1 | 1/2022 | |

OTHER PUBLICATIONS

Examination Report for EPO Application No. 17864205.4 dated May 19, 2020.
PCT Search and Patentability Report for PCT/US2016/21763, dated Jun. 2, 2016.
PCT Search and Patentability Report for PCT/US2017/58736, dated Jan. 5, 2018.
PCT Search and Patentability Report for PCT/US2017/21833, dated Jun. 9, 2017.
Le Metayer-Levrel G, et al, "Applications of bacterial carbontogeesis to the protection and regeneration of limestones in building and historic patrimony," Sedimentary Geology, Jul. 31, vol. 126, No. 1, pp. 26, 29, 32-33 (1999).
PCT International Search Report; PCT/US0211/033920; dated Jul. 22, 2011; Dosier, Ginger Krieg.
Day, Jeremy L. et al, Microbiologically Induced Sealant for Concrete Crack Remediation, http://www.ce.washingtonedu/em2003/proceedings/papers/352.pdf.
Dejong, Jason T. et al, Bio-mediated Soil Improvement; Ecological Engineering, 2009, pp. 197-210, vol. 36, Elsevier.
Dejong, Jason T. et al, Microbially Induced Cementation to Control Sand Response to Undrained Shear, Journal of Geotechnical and Geoenvironmental Engineering, Nov. 2006, pp. 1381-1392, ASCE.
Ferris, F.G. et al, Bacteriogenic Mineral Plugging, Petroleum Society of CIM and CANMET, Paper No. 11, pp. Nov. 11-11-12.
Fritzges, Michael B. et al, Biologically Induced Improvement of Loose Sand, Proceedings of the 8th U.S. National Conference on Earthquake Engineering, Apr. 18-22, 2006, Paper No. 1691, San Francisco, US.
Gollapudi, U.K. et al, A New Method for Controlling Leaching Through Permeable Channels, Chemosphere, 1995, pp. 695-705, vol. 30, No. 4, Elsevier Science Ltd., Great Britain.
Kantzas, A. et al, A Novel Method of Sand Consolidation Through Bacteriogenic Mineral Plugging, Petroleum Society of CIM, Jun. 7-10, 1992, pp. 46-1-46-15, Paper No. CIM 92-46.
De Muynck, Willem et al, Microbial Carbonate Precipitation in Construction Materials: A Review, Ecological Engineering, 2010, pp. 118-136, vol. 36, Elsevier.

(56) References Cited

OTHER PUBLICATIONS

Nemati, M. et al, Modification of Porous Media Permeability, Using Calcium Carbonate Produced Enzymatically In Situ, Enzyme and Microbial Technology, 2003, pp. 635-642, vol. 33, Elsevier.
Stocks-Fischer, Shannon et al, Microbiological Precipitation of CaCO3, Soil Biology and Biochemistry, 1999, pp. 1563-1571, vol. 31, Elsevier Science Ltd.
Whiffin, Victoria S. et al, Microbial Carbonate Precipitation as a Soil Improvement Technique, Geomicrobiology Journal, 2007, pp. 417-423, vol. 24, Taylor & Francis Group, LLC.
Whiffin, Victoria S., Microbial CaCO3 Precipitation for the Production of Biocement, PhD Thesis, 2004, Murdoch University, Western Australia.
Examination Report for CN Application No. 201780067243.9 dated Feb. 10, 2021.
Examination Report for CN Application No. 201780067243.9 dated Feb. 10, 2021—translation.
Achal, Varenyam, et al., "Biogenic Treatment Improves the Durability and Remediates the Cracks of Concrete Structures", Construction and Building Materials, 2013, vol. 48, pp. 1-5.
BioZEment (completed). Web Page. UiO Department of Physics. Published Nov. 3, 2014. Last modified Nov. 27, 2017. Retrieved Oct. 22, 2021 at URL: https://www.mn.uio.no/fysikk/english/research/projects/biozement/. 5 pages.
Choi, Sun-Gyu, et al., "Biocementation for Sand Using an Eggshell as Calcium Source", Journal of Geotech, Journal of Geotechnical and Geoenvironmental Engineering, Technical Note, 2016, pp. 1-4.
Choi, Sun-Gyu, et al., "Properties of Biocemented, Fiber Reinforced Sand", Construction and Building Materials, 2016, vol. 120, pp. 623-629.
Chu, Jian, et al., "Proof of Concept: Biocement for Road Repair", Final Report, Mar. 2015, Iowa State University, Midwest Transportation Center, 15 Pages.
Chu, Jian, "Solutions to Sustainability in Construction: Some Examples", Procedia Engineering, 2016, vol. 145, pp. 1127-1134.
Cunningham, A.B., et al., "Reducing the Risk of Well Bore Leakage of CO2 Using Engineered Biomineralization Barriers", Energy Procedia, 2011, vol. 4, pp. 5178-5185.
Fujita, Yoshiko, et al., Evaluating the Potential of Native Ureolytic Microbes to Remediate a 90Sr Contaminated Environment, Environmental Science & Technology, 2010, vol. 44, No. 19, pp. 7652-7658.
Ghosh, P., et al., "Use of Microorganism to Improve the Strength of Cement Mortar", Cement and Concrete Research, 2005, vol. 35, pp. 1980-1983.
Hammes et al. Key roles of pH and calcium metabolism in microbial carbonate precipitation. Re/Views in Environmental Science & Bio/Technology 1:3-7 (2002).
Jonkers, Henk M., et al., "A Two Component Bacteria-Based Self-Healing Concrete", Proceedings of the 2nd International Conference on Concrete Repair, Rehabilitation and Retrofitting (ICCRRR), Cape Town, South Africa, Nov. 24-26, 2008. Concrete Repair, Rehabilitation and Retrofitting II, pp. 119-120, Taylor & Francis Group, London.
Kim et al. Calcium Carbonate Precipitation by Bacillus and Sporosarcina Strains Isolated from Concrete and Analysis of the Bacterial Community of Concrete. J. Microbiol. Biotechnol. (2016), 26(3), 540-548. First published online Dec. 23, 2015.
Phua, Y.J., et al., "Morphology and Polymorphism of Calcium Carbonate Precipitated from Different Calcium Sources via Enzyme Induced Carbonate Precipitation", Department of Physics, University of Oslo, Norway, 2016, Goldschmidt Conference Abstracts—1 Page.
Rodriguez-Navarro, Carlos, et al., "Influence of Substrate Mineralogy on Bacterial Mineralization of Calcium Carbonate: Implications for Stone Conservation", Applied and Environmental Microbiology, Jun. 2012, vol. 78, No. 11, pp. 4017-4029.
Stabnikov, Viktor, et al., "Halotolerant, Alkaliphilic Urease-Producing Bacteria from Different Climate Zones and their Application for Biocementation of Sand", World Journal of Microbiology and Biotechnology, 2013, vol. 29, pp. 1453-1460.
Sun et al. Study of magnesium precipitation based on biocementation. Marine Georesources & Geotechnology, 2019, vol. 37, No. 10, pp. 1257-1266. Published online Jan. 29, 2019.
Van Paassen, Leon A., et al., "Potential Soil Reinforcement by Biological Denitrification", Ecological Engineering, 2010, vol. 36, pp. 168-175.
Zander, R., et al., "Association Between Plasma Ionized Calcium and Lactate Concentration", Intensive Care Medicine, 1993, vol. 19, No. 6, pp. 362-363.
Application of Bacteria as Self-Healing Agent for the Development of Sustainable Concrete, H.M. Jonkers et al., Ecological Engineering 36:230-235, 2010.
Bang et al., "Calcite precipitation induced by polyurethane immobilized Bacillus pasteurii", Enzyme and Microbial Technology, 2001, vol. 28, pp. 404-409.
Bundur et al., Biomineralized cement-based materials: impact of inoculating vegetative bacterial cells on hydration and strength. Cement and Concrete Res., 2015, vol. 67: 237-245. Available online Oct. 27, 2014.
Castro-Alonso et al., Microbially Induced Calcium Carbonate Precipitation (MICP) and Its Potential in Bioconcrete: Microbiological and Molecular concepts. Frontiers in Materials, 2019, vol. 6, Article 126: 1-15.
Chekroun et al. Precipitation and Growth Morphology of Calcium Carbonate Induced by Myxococcus Xanthus: Implications for Recognition of Bacterial Carbonates. Journal of Sedimentary Research 74 (6): 868-876 (2004).
Cho et al., "Effect of Surfactants on CO2 Biomineralization with *Sporosarcina pasteurii* and *Bacillus megaterium*", Water Air Soil Pollut., 2015, vol. 226:2245, pp. 1-12.
Cichoż-Lach et al. Current pathogenetic aspects of hepatic encephalopathy and noncirrhotic hyperammonemic encephalopathy. World J Gastroenterol. Jan. 7, 2013;19(1):26-34.
CN201780067243.9 Office Action and Search Report dated Feb. 10, 2021 (w/ English summary).
Co-pending U.S. Appl. No. 16/933,171, inventors Hill; Thomas A. et al., filed Jul. 20, 2020.
Co-pending U.S. Appl. No. 17/322,179, inventors Dosier; Ginger K. et al., filed May 17, 2021.
Cuzman et al., Bacterial "Masons" at work with wastes for producing eco-cement. Int. J. Environ. Sci. Develop., 2015, vol. 6(10): 767-774.
Day, Jeremy L. et al, Microbiologically Induced Sealant for Concrete Crack Remediation, https://www.ce.washingtonedu/em2003/proceedings/papers/352.pdf (2003).
EP17864205.4 Extended European Search Report dated May 29, 2020.
F. D. Meyer et al, "Microbiologically-Induced Soil Stabilization: Application of *Sporosarcina pasteurii* for Fugitive Dust Control", GEO-Frontiers 2011, Reston, VA, (Mar. 11, 2011), doi:10.1061/41165(397)409, ISBN 978-0-7844-1165-0, pp. 4002-4011, XP055562331.
Ferris, F.G. et al, Bacteriogenic Mineral Plugging, Petroleum Society of CIM and CANMET, Paper No. 11, presented at the CIM/CANMET Fourth Petroleum Conference held in Regina, Sask., pp. 11-1 to 11-12, Oct. 7-9, 1991.
Fukue et al, Grain growth of carbonates using ureolytic microbes, Japanese Geotechical Journal, (2011), vol. 6, No. 3, pp. 455-464, with English translation of abstract.
Gleb B. Sukhorukov et al., "Porous calciumcarbonate microparticles as templates for encapsulation of bioactive compounds" J. Mater. Chem. 14:2073-2081, 2004.
Ivanov et al, "Calcite/aragonite-biocoated artificial coral reefs for marine parks", AIMS Environmental Science, Aug. 22, 2017, vol. 4 (4), pp. 586-595.
Ivanov et al., Chapter 7, Biocementation and Biocements. Construction Biotechnol., Green Energy and Technol., Chapter 7, 2017, pp. 109-138.
Kalantary et al., Evaluation of the ability to control biological precipitation to improve sandy soils. Procedia Earth. Planet. Sci., 2015, vol. 15:278-284.

(56) References Cited

OTHER PUBLICATIONS

Kim et al. Microbially mediated calcium carbonate precipitation on normal and lightweight concrete. Construction and Building Materials, vol. 38, pp. 1073-1082 (2013). Available online Nov. 6, 2012.
Kurizaki et al, "A Case of Stone Formation in the Mainz Pouch using Appendix as the Efferent Limb: A Case Report", Nihon Hinyokika Gakkai Zasshi. The Japanese Journal of Urology, 2002, vol. 93(4), pp. 573-576. (English translation of abstract.).
Ibtisam A. Hammad et al., Urease activity and induction of calcium carbonate precipitation by Sporosarcina pasteurii NCIMB 8841; Journal of Applied Sciences Research 9(3): 1525-33, 2013.
Mazria. It's the Architecture, Stupid! pp. 48-51. Retrieved Aug. 29, 2021 from URL: https://backspace.com/notes/images/its_the_architecture.pdf. May/Jun. 2003.
Metayer-Levrel et al., Applications of bacterial carbonatogenesis to the protection and regeneration of limestones in buildings and historic patrimony. Sedimentary Geology., 1999, vol. 126: 25-34.
Meyer et al., "Microbiologically-Induced Soil Stabilization: Application of Sporosarcina pasteurii for Fugitive Dust Control", Geo-Frontiers Congress 2011, pp. 4002-4011.
Park et al., "Effect of Plant-Induced Calcite Precipitation on the Strength of Sand", Journal of Materials in Civil Engineering, 2014, vol. 26, Issue 8.
PCT/US2011/033920 International Search Report and Written Opinion dated Aug. 2, 2011.
PCT/US2017/058736 International Preliminary Report on Patentability dated Apr. 30, 2019.
PCT/US2017/058736 Written Opinion dated Jan. 5, 2018.
Phillips A.J., Biofilm-induced calcium carbonate precipitation: Application in the subsurface. Ph.D., Dissertation, Montana State University, Nov. 2013, pp. 1-241.
Phillips et al., Engineered applications of ureolytic biomineralization: a review. Biofouling, 2013, vol. 29(6): 715-733.
Pinar et al, "Bacterial Community Dynamics During the Application of a *Myxococcus xanthus*—Inoculated Culture Medium Used for Consolidation of Ornamental Limestone", Microb.Ecol., 2010, vol. 60, pp. 15-28.
Reddy et al. Embodied energy of common and alternative building materials and technologies. Energy and Buildings, vol. 35, Issue 2, pp. 129-137 (2003).
Remediation of Concrete Using Microorganisms, S.K. Ramachandran et al., ACI Materials Journal Jan./Feb. 2001.
Romillac N., Ammonification. Encyclopedia of Ecology, 2nd edition, 2019, vol. 2: 256-263.
Stabnikov et al., "Immobilization of Sand Dust and Associated Pollutants Using Bioaggregation", Water, Air, & Soil Pollution, 2013, vol. 224, 1631.
Streamer, M., "Urea and Arginine metabolism in the Hard Coral, Acropora acuminata", Comp. Biochem. Physiol., vol. 65B, pp. 669 to 674, 1980.
Talaiekhozani et al., "Application of Proteus mirabilis and Proteus vulgaris mixture to design self-healing concrete", Desalination and Water Treatment, 2014, vol. 52, pp. 3623-3630.
The Better Brick, 2010 Next Generation Winner (https://www.metropolismag.com/uncategorized/the-better-brick-2010-next-generation-winner/).
Therkildsen et al., Urea production by the marine bacteria *Delaya venusta* and *Pseudomonas stutzeri* grown in minimal medium, Aquatic Microbial Ecology, vol. 13:213-217 (1997).
Through the Sandglass, (http://throughthesandglass.typepad.com/through_the_sandglass/2010/07/sandbacteriaurinebricks-continuing-performances-of-bacillus-pasteurii.html) Jul. 19, 2010.
T.K. Ghose et al., "Studies on fibre-entrapped whole microbial cells in urea hydrolysis," Enzyme and Microbial Technology, vol. 1, No. 1, pp. 47-50, Jan. 1, 1979.

Wang et al., Application of microorganisms in concrete: a promising sustainable strategy to improve concrete durability. Appl. Microbial Biotechnol., 2016, vol. 100: 2993-3007.
Wikipedia, "Shale," Aug. 22, 2018; retrieved on Sep. 13, 2021 from https://en.wikipedia.org/w/index.php?title=Shale&oldid=855968675.
Wikipedia, "Pseudomonas fluorescens," May 15, 2018; retrieved on Sep. 13, 2021 from https://en.wikipedia.org/w/index.php?title-Pseudomonas_fluorescens&oldid=841444300.
Wiktor et al., Quantification of crack-healing in novel bacteria-based self-healing concrete. Cement & Concrete Composites, 2011, vol. 33: 763-770.
Yoosathaporn et al., The influence of biocalcification on soil-cement interlocking block compressive strength. Biotechnol. Agron. Soc. Environ.,2015, vol. 19 (3): 262-269.
Zeolite as a Binding Agent for Ammonia Ions and as a Soil Additive. Part 1 Amonnia Adsorption by the Zeolite, Proceedings of the 5th Serbian-Croatian-Slovenian Symposium on Zeolites, J. Milovanovic et al., May 2013.
Zeynep Basaran Bundur et al., Biomineralized cement-based materials: Impact of inoculating vegetative bacterial cells on hydration and strength, Cement and Concrete Research 67:237-245 (2015). (Available online Oct. 27, 2014).
Zhao et al., Bioremediation of Cd by strain GZ-22 isolated from mine soil based on biosorption and microbially induced carbonate precipitation. Environ. Sci Pollut Res., 2017, Vo. 24: 372-380.
Beck et al. On the use of eggshell lime and tuffeau powder to formulate an appropriate mortar for restoration purposes. From Smith et al., eds. Limestone in the Built Environment: Present-Day Challenges for the Preservation of the Past. Geological Society, London, Special Publications, 331, 137-145 (Jan. 1, 2010).
Cree et al. Sustainable Bio-Inspired Limestone Eggshell Powder for Potential Industrialized Applications. ACS Sustainable Chem Eng 3, 941-949 (Apr. 9, 2015).
Ivanov et al. Sustainable and Safe Construction Biomaterials: Biocements and Biogrouts. Frontiers in Biomaterials, vol. 6, pp. 177-193 (2019).
Karthik et al. Properties of Bacterial-based Self-healing Concrete—A review. International Journal of ChemTech Research, vol. 9, No. 2, pp. 182-188 (2016).
Mendz et al. The urea cycle of Helicobacter pylori. Microbiology 142, 2959-2967 (1996).
Pedersen et al. Evidence for bacterial urea production in marine sediments. FEMS Microbiology Ecology 12, 51-59 (1993).
Van Paassen et al. Scale up of BioGrout: a biological ground reinforcement method. Hamza et al., ed. Proceedings of the 17th International Conference on Soil Mechanics and Geotechnical Engineering, IOS Press, pp. 2328-2333 (2009).
Vijay et al. Bacteria based self healing concrete—A review. Construction and Building Materials 152:1008-1014 (2017). Available online Jul. 15, 2017.
Wei et al. Biomineralization processes of calcite induced by bacteria isolated from marine sediments. Brazilian Journal of Microbiology 46, 2, 455-464 (2015).
CN202210666353.X Search Report dated Feb. 10, 2023 (w/ English translation).
Co-pending U.S. Appl. No. 17/822,067, inventors Hill; Thomas A. et al., filed Aug. 24, 2022.
Co-pending U.S. Appl. No. 18/178,078, inventors Hill; Thomas A. et al., filed Mar. 3, 2023.
Co-pending U.S. Appl. No. 18/178,082, inventor Dosier; Ginger K., filed Mar. 3, 2023.
Examination Report for EPO Application No. 17864205.4 dated Jan. 25, 2021.

\* cited by examiner

MICROORGANISM LOADED AGGREGATE AND MANUFACTURING METHODS

REFERENCE TO RELATED APPLICATIONS

This Application claims priority to U.S. Provisional Application No. 62/414,876 filed Oct. 31, 2016, which is entirely incorporated by reference.

BACKGROUND

1. Field of the Invention

The invention is directed to compositions, tools and methods for the manufacture of construction materials. More particularly, the invention is directed to the manufacture of bricks, masonry and other solid structures, and dust control using aggregate materials loaded with spores and/or vegetative microorganisms to initiate and/or standardize the manufacturing process which may be utilized in large-scale production.

2. Description of the Background

Traditional brick and concrete construction is heavily reliant on burning natural resources such as coal and wood. This reliance results in the consumption of massive amounts of energy resources and equally massive carbon dioxide emissions, thus a great dependency on limited energy sources. An alternative to these traditional processes involves a process known as microbial induced calcite precipitation (MICP). MICP comprises mixing urease and urea as a source of energy with an aggregate material such as, for example, sand. The enzyme catalyzes the production of ammonia and carbon dioxide, increasing the pH level of the composition. The rise in pH forms a mineral "precipitate," combining calcium with carbon dioxide. Particles present in the mixture act as nucleation sites, attracting mineral ions from the calcium forming calcite crystals. The mineral growth fills gaps between the sand particles biocementing or bonding them together. Preferably, the particles contain gaps of at least 5 microns in width, but can be larger or smaller as desired. The resulting material exhibits a composition and physical properties similar to naturally formed masonry, bricks or other solid structures. Hardness can be predetermined based at least on the structure of the initial components and the pore size desired.

Enzyme producing bacteria that are capable of biocementation include *Sporosarcina ureae*, *Proteus vulgaris*, *Bacillus sphaericus*, *Myxococcus xanthus*, *Proteus mirabilis*, or *Helicobacter pylori*, although proper concerns should be given to pathogenic strains. Combinations of any of these strains as well as functional variants, mutations and genetically modified stains may be used as well. Bacterial compositions contain nutrient media to maintain and/or allow the cells to flourish and proliferate. The various types of nutrient media for cells, and in particular, bacterial cells of the invention are known and commercially available and include at least minimal media (or transport media) typically used for transport to maintain viability without propagation, and yeast extract, and molasses, typically used for growth and propagation.

This method for manufacturing construction materials through induced cementation exhibits low embodied energy, and can occur at ambient pressure, and in a wide range of temperatures. The ambient temperature and conditions as well as the content of available aggregate can determine whether pure enzyme, lyophilized enzyme, or live cells are utilized as the starting components. Generally, live cells are used in warmer temperatures where mild weather conditions exist, whereas pure enzymes can be advantageous at more extreme conditions of cold or heat. The introduction of a bioengineered building unit using sand aggregate and naturally induced cementation provides a natural alternative that may be locally produced and environmentally friendly. As little to no heating is necessary, the energy savings in both expenses and efficiency is enormous.

The initial ingredients needed for MICP are readily available. Sources of calcium are often locally available from, for example, local geology such as limestone, milk and milk products and by-products, egg shells, lakes and rivers, sea water, and plant materials to name a few. Calcium is used as a source when in the form of a salt such as, preferably, calcium chloride, calcium carbonate, calcium lactate, calcium acetate, calcium phosphate and calcium sulfate. Many of these forms are readily available in different parts of the world. Also readily available in most parts of the world is urea. As a chemical salt, it can be easily obtained from urine which is available from livestock and agricultural sources, as well as municipal sources. Thus, compositions of the invention may include a calcium source and/or urea, and/or the calcium source and/or urea may be obtained separately.

Another advantage of MICP is that the process can be utilized in both small and large scale, and also easily automated. The bulk content of the masonry manufacturing process of the invention can be most any material that is locally available including rocks, sand, gravel and most any type of stone. Processing of the stone, such as crushing or breaking into pieces, also can be performed locally. Thus, transport costs and expenses are minimized The composition of the invention (which may be provided lyophilized and hydrated on site), the frame for the bricks (if otherwise unavailable), and instructions as appropriate are all that need to be provided. If shipping is required, this represents a tiny fraction of the delivery costs, especially as compared to the present expenses associated with the delivery of conventional cement.

Another advantage of this invention is to produce a "grown" construction material, such as a brick, utilizing primarily minerals, MICP and loose aggregate, such as sand. Not only can bricks and other construction materials be created, but the bricks themselves can be cemented into the desired places using the composition of the invention to "cement" the bricks to one another and/or to other materials thereby forming the buildings, support structure or member, walls, roads, and other structures.

Biologically grown bricks and masonry do not require the traditional use of Portland cement mortar, which enables the reduction of atmospheric carbon dioxide by offering an alternative to the high-embodied energy traditionally manufactured construction materials. Employing cells to naturally induce mineral precipitation, combined with local aggregate and rapid manufacturing methods enables the production of a local, ecological, and economic building material for use throughout the global construction industry.

Although MICP can be utilized to create nearly any form of brick, block or solid structure used in construction, efficient methods for large scale manufacture have yet to be developed. Thus, a need exists for a rapid and convenient process that provides consistency to the manufacture of masonry that is both economical and environmentally safe.

SUMMARY OF THE INVENTION

The present invention overcomes problems and disadvantages associated with current strategies and designs, and provides new tools, compositions, and methods for the manufacture of building materials.

One embodiment of the invention is directed to methods comprising: adding an aqueous medium to a collection of viable spore-forming bacteria forming an aqueous mixture; incubating the aqueous mixture under conditions that promote or specifically induce spore formation or vegetative cell formation; mixing spores and/or vegetative cells with aggregate particles forming a slurry; and concentrating the spores and/or vegetative cells by removing at least a portion of liquid which is mostly water. Preferably the aqueous medium is at a physiological pH, promotes spore formation, comprises one or more of salts, amino acids, proteins, peptides, carbohydrates, saccharides, polysaccharides, fatty acids, oil, vitamins and minerals, and does not contain urea. Preferably the viable spore-forming bacteria comprise one or more strains of *Sporosarcina pasteurii, Sporosarcina ureae, Proteus vulgaris, Bacillus sphaericus, Myxococcus xanthus, Proteus mirabilis, Bacillus megaterium, Helicobacter pylori,* and/or any urease and/or carbonic anhydrase producing microorganism. Preferably incubating is performed at from about 25-40° C. and for about 6 hours to about 6 days, more preferably for about 1-3 days. Preferably mixing further includes addition of a binding agent. Preferred binding agents promotes adhesion between spores and/or vegetative cells and aggregate via, for example, hydrophobic bonds, hydrophilic bonds, ionic bonds, non-ionic bonds, covalent bonds, van der Waal forces, or a combination thereof, and may comprise a polymer, a saccharide, a polysaccharide, a carbohydrate, a fatty acid, an oil, an amino acid, or a combination thereof. Preferred aggregate particles comprise natural, non-natural, recycled or manufactured sand, ore, crushed rock or stone, minerals, crushed or fractured glass, mine tailings, paper, waste materials, waste from a manufacturing process, plastics, polymers, roughened materials, and/or combinations thereof, wherein aggregate particles are in the form of beads, grains, strands, fibers, flakes, crystals, or combinations thereof. Preferred particle sizes or average diameters will pass through a mesh size of 100 or smaller, or more preferably a mesh size is 200 or smaller. Removal of an aqueous component is preferably accomplished by evaporation, heat-assisted evaporation, filtration and/or vacuum-assisted filtration and/or an aqueous liquid may be added to the concentrated slurry. Preferably the slurry contains from about $10^{10}$ to about $10^{15}$ spores and/or vegetative cells/ml.

Another embodiment of the invention comprises spore-loaded aggregate made by the methods of the invention. Preferably the spore-loaded aggregate contains less than about 50% liquid by weight, less than about 10% liquid by weight, less than about 5% liquid by weight, or no liquid. Spore-loaded aggregate or dried spore-loaded aggregate may be supplemented with additional aqueous liquid, such as but not limited to water, PBS or saline. Preferably spore-loaded aggregate contains from about $10^6$ to about $10^{12}$ spores and/or vegetative cells/ml.

Another embodiment of the invention is directed to method of manufacturing construction material, solid structures, or the manufacture of compositions to utilize for dust control applications comprising: combining in any order a spore-loaded aggregate composition of the invention with urea, calcium, additional aggregate material, which may be the same or different, and an incubation medium forming a mixture; incubating the mixture under conditions that promote formation of calcium carbonate; and forming the construction material. Incubation of the mixture may be in a formwork, which may be a fixed or powdered solid material, or after extrusion in the absence of a formwork. Preferably the construction material comprises bricks, thin bricks, pavers, panels, tile, veneer, cinder, breeze, besser, clinker or aerated blocks, counter- or table-tops, design structures, blocks, or a solid masonry structure. Also preferably the calcium is provided from calcium chloride, calcium acetate, calcium phosphate, calcium carbonate, calcium lactate, calcium nitrate, or a calcium salt, the aggregate material comprises natural, non-natural, recycled or manufactured sand, ore, crushed rock or stone, minerals, crushed or fractured glass, wood, ash, foam, basalt, fibers, mine tailings, paper, waste materials, waste from a manufacturing process, plastics, polymers, roughened materials, and/or combinations thereof, and incubation promoting proliferation of urease-producing vegetative cells.

Another embodiment of the invention is construction material and dust control compositions manufactured by the methods of this disclosure.

Other embodiments and advantages of the invention are set forth in part in the description, which follows, and in part, may be obvious from this description, or may be learned from the practice of the invention.

DESCRIPTION OF THE INVENTION

The manufacture of masonry and other building materials using a process known as microbial induced calcite precipitation (MICP) has been extensively described in a number of U.S. Patent (e.g., see U.S. Pat. Nos. 8,728,365; 8,951,786; 9,199,880; and 9,428,418; each of which is incorporated in its entirety by reference). In these processes, urease-producing cells or urease enzymes are mixed with aggregate and incubated with urea and a calcium source. Calcite bonds form between aggregate particles resulting in a solid structure. Although the process allows for the manufacture of building materials, manufacturing generally requires standardization for the purpose of large-scale production.

It has been surprisingly discovered that the manufacture of biologically-created solids can be standardized and, accordingly the manufacturing process enhanced. Standardization is achieved by adding an aqueous medium to a collection of viable spore-forming bacteria forming an aqueous mixture and incubating the aqueous mixture under conditions that promote spore formation. Spores of most urease-producing microorganisms are generally round, oval or slightly elongated with sizes from about 0.9 µm to 2.0 µm in length and from about 0.5 µm to about 1.0 µm in width. Spores and/or vegetative cells are then mixed with aggregate particles, preferably but not necessarily aggregate consistent with and/or similar to the bulk aggregate, forming a slurry and the slurry concentrated by the removal of at least a portion of the aqueous component, essentially the water, but not the spores and/or vegetative cells. Retention of spores and/or vegetative cells can be achieved by utilizing aggregate particles of a size or average size and composition that permits the transference of liquid such as water but retains spores and/or vegetative cells. These ultrafine aggregate particles can be maintained as a slurry or further liquid can be removed as desired to form a powder or solid structure.

One embodiment of the invention is directed to a method for forming starter cultures of spores and/or vegetative cells and aggregate material for the manufacture of solid structures, construction materials, or the manufacture of compositions to utilize for dust control applications (e.g., U.S. Pat. No. 8,951,786 issued 10 Feb. 2015; U.S. Pat. No. 9,428,418 issued 30 Aug. 2016; U.S. Patent Application Publication No. 2016/0264463 entitled "Compositions and Methods for Dust Control and the Manufacture of Construction Materials" published 16 Sep. 2016; U.S. Patent Application Publication No. 2016/0362334; each of which is entirely incorporated by reference). Spores and vegetative cells can be cultured from spore-producing bacterial and/or may be previously prepared and, preferably, under conditions that specifically induce the formation or spores or vegetative cells. The resulting solution or spore-containing or cell-containing culture is mixed with aggregate particles forming a slurry. Spores and/or vegetative cells (microorganisms) are concentrated from the slurry by removing at least a portion of liquid. Preferably the aggregate particles are largely or completely of a mesh size of 100 or smaller (particles of 150 μm or smaller), more preferably 200 or smaller (particles of about 75 μm or smaller) and more preferably 300 or smaller (particles of about 38 μm or smaller). Generally, particle sizes are measured or determined as average sizes. Water and dissolved aqueous materials can be removed and the microorganisms remain within the aggregate. In this way aggregate material can be loaded with a desired amount or quantity of microorganisms and stored. The microorganism-loaded aggregate particles can be maintained as a slurry, or dried as a powder or solid form. As the mixture contains aggregate and microorganisms, the mixture is relative resistant to variations in temperature or most any other external conditions, and therefore can be maintained for long periods of time. In this way, large numbers of spores and/or vegetative cells can be maintained to coordinate large manufacturing operations.

In a first step, spore-forming bacteria are cultured, preferably under conditions that promote spore and/or vegetative cell formation. Culture conditions include an aqueous medium comprising one or more of salts, amino acids, proteins, peptides, carbohydrates, saccharides, polysaccharides, fatty acids, oil, vitamins and minerals. Preferably, the aqueous medium does not contain urea, which will stimulate spore formation of the bacteria. Preferred spore-forming bacteria comprise one or more strains of *Sporosarcina pasteurii, Sporosarcina ureae, Proteus vulgaris, Bacillus sphaericus, Myxococcus xanthus, Proteus mirabilis, Bacillus megaterium, Helicobacter pylori*, and/or any urease and/or carbonic anhydrase producing microorganism. Bacteria are cultured in the aqueous medium, preferably at incubation is at a physiological pH and at temperatures of from about 25-40° C. Preferably incubation is performed from about 6 hours to about 6 days, more preferably for about 1-3 days, or as short a time as necessary to generate the desired number of spores and/or vegetative cells per bacterium.

Preferably spore formation or vegetative cell formation is induced, although an induction step is not required, and the microorganisms may be centrifuged or otherwise concentrated, and preferably resuspended into a paste with media or another suitable liquid that maintains the microorganisms without inducing further growth and/or proliferation (a status solution). Alternatively, microorganisms may be need mixed with aggregate without concentration, which may be preferable for manufacturing batches of vegetative cells.

Following spore-formation or vegetative cell formation as desired, cultures are mixed with aggregate particles. Aggregate particles may comprise natural, non-natural, recycled or manufactured sand, ore, crushed rock or stone, minerals, crushed or fractured glass, mine tailings, paper, waste materials, waste from a manufacturing process, plastics, polymers, roughened materials, and/or combinations thereof, and may be in the form of beads, grains, strands, fibers, flakes, crystals, or combinations thereof. Preferably the aggregate particles comprise particles with a mesh size of 100 or smaller (particles of about 150 μm or smaller), more preferably with a mesh size is 200 or smaller (particles of about 75 μm or smaller), or more preferably with a mesh size of 300 or smaller (particles of about 38 μm or smaller).

Preferably the aqueous mixture of spores and/or vegetative cells and/or the aggregate is combined with a binding agent that promotes the adhesion or retention of microorganisms and aggregate. Adhesion may be between microorganisms and aggregate via hydrophobic bonds, hydrophilic bonds, ionic bonds, non-ionic bonds, covalent bonds, van der Waal forces, or a combination thereof. Binding agents include, but are not limited to one or more of polymers, saccharides, polysaccharides, carbohydrates, fatty acids, oils, amino acids, or combinations thereof. Preferred binding agents are nontoxic and/or biodegradable and also preferably harmless to the spores and do not interfere or otherwise hinder eventual germination of spores or proliferation of vegetative cells.

Preferably the aqueous component and mixture is removed is by evaporation and/or filtration, such as, for example, heat-assisted evaporation, pressure-assisted filtration, and/or vacuum-assisted filtration. Following evaporation and/or filtration, the slurry or aggregate particles and microorganisms contains from about $10^6$ to about $10^{14}$ spores and/or cells/ml, preferably from about $10^8$ to about $10^{12}$, and more preferably from about $10^9$ to about $10^{11}$. The aqueous component can be further removed or removed entirely without hard to the spores and/or vegetative cells and the dried powder or block stored for future use in starting a culture of urease-producing bacteria.

Spore-containing aggregate material has a very long shelf life with greater than 80% viability after months and/or years with proper storage conditions. Vegetative-containing aggregate has a somewhat shorter shelf life with greater than 80% remaining viable after months and longer with proper storage conditions.

Another embodiment of the invention is directed to a composition comprising spore-loaded aggregate made by the methods of the invention. Preferably aggregate particles are of a mesh size of 100 or smaller (particles of about 150 μm or smaller), 200 or smaller (particles of about 75 μm or smaller), or 300 or smaller (particles of about 38 μm or smaller). Also preferably, the composition contains a binding or retention agent. The binding agent promotes adhesion between spores and/or vegetative cells and aggregate particles and/or the retention agent increases the size of aggregate particles and/or spores and/or vegetative cells, which promotes their retention.

Preferably the composition contains less than about 50% liquid by weight, more preferably less than about 10% liquid by weight, and more preferably less than about 5% liquid by weight. Preferred compositions contain from about $10^{19}$ to about $10^{15}$ spores and/or vegetative cells/ml.

Another embodiment of the invention is directed to methods of manufacturing construction material comprising combining in any order compositions of the invention with urea, calcium, an aggregate material, and an incubation medium forming a mixture. The mixture is incubated under conditions that promote formation of calcium carbonate which forms the solid structure of aggregate materials. Preferred solid structures include, for example, construction materials such as bricks, thin bricks, pavers, panels, tile, veneer, cinder, breeze, besser, clinker or aerated blocks, counter- or table-tops, design structures, blocks, or a solid masonry structure. Preferably the calcium is provided from calcium chloride, calcium acetate, calcium phosphate, calcium carbonate, calcium lactate, calcium nitrate, or a calcium salt. Also preferably the aggregate material comprises natural, non-natural, recycled or manufactured sand, ore, crushed rock or stone, minerals, crushed or fractured glass, wood, ash, foam, basalt, fibers, mine tailings, paper, waste materials, waste from a manufacturing process, plastics, polymers, roughened materials, and/or combinations thereof. Solid structures can be formed in a formwork or extruded as desired. Extruded aggregate retains a basic shape upon extrusion that solidifies over time into a solid structure at a desired hardness.

The following examples illustrate embodiments of the invention, but should not be viewed as limiting the scope of the invention.

EXAMPLES

Example 1

Spore Production

Sporosarcina pasteurii spores were produced from vegetative cells in culture media.

Example 2

Spore Loading

Spores (approximately 1 μm in diameter) were directly loaded into aggregate fines either by (1) vacuum-assisted or pressure-assisted filtration (or simply gravity assisted), or (2) evaporation. Alternatively, spore cultures may be concentrated and stored refrigerated in phosphate buffered saline (PBS) until ready for loading.

Method 1: Vacuum-Assisted Filtration
1. Whole spore cultures (2 L) were mixed with 1 kg ultrafine (<75 μm avg. diameter) manufactured aggregates.
2. A filtering apparatus was applied and the vacuum or a pressure engaged to facilitate liquid clearance.
3. Loaded fines were harvested and dried completely.

Method 2: Evaporation
1. Whole spore cultures (2 L) were mixed with 1 kg ultrafine (<75 μm avg. diameter) mining aggregates.
2. Spore aggregate mixtures were spread evenly over maximum surface area and dried under circulating air.
3. Loaded fines were harvested and dried completely.

Spore loading aggregate from Method 1 demonstrated high retention of dormant spores within crude aggregate. Method 2 yielded a similar spore to aggregate distribution.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:
1. A method of manufacturing a shelf-stable spore-loaded aggregate, the method comprising:
(a) adding an aqueous medium to a collection of viable spore-forming bacteria to form an aqueous mixture;
(b) incubating the aqueous mixture under conditions that promote the formation of spores and/or vegetative cells;
(c) mixing the aqueous mixture incubated in (b) with aggregate particles; and
(d) removing at least a portion of the aqueous medium to concentrate the spores or vegetative cells with the aggregate particles: (i) to a concentration of $10^6$ to $10^{15}$ cells/mL and (ii) until the mixture contains less than 50% liquid by weight, to provide the shelf stable spore-loaded aggregate, which remains at least 80% viable after months of storage.

2. The method of claim 1, wherein the aqueous medium comprises one or more of salts, amino acids, proteins, peptides, carbohydrates, saccharides, polysaccharides, fatty acids, oil, vitamins and minerals.

3. The method of claim 1, wherein the aqueous medium does not contain urea.

4. The method of claim 1, wherein the viable spore-forming bacteria comprise one or more strains of *Sporosarcina pasteurii, Sporosarcina ureae, Proteus vulgaris, Bacillus sphaericus, Myxococcus xanthus, Proteus mirabilis, Bacillus megaterium, Helicobacter pylori*, and/or a urease and/or a carbonic anhydrase producing microorganism.

5. The method of claim 1, wherein the incubating is performed at from 25-40° C.

6. The method of claim 1, wherein the incubating is performed from 6 hours to 6 days.

7. The method of claim 6, wherein the incubating is performed for 1-3 days.

8. The method of claim 1, wherein the conditions comprise a physiological pH.

9. The method of claim 1, wherein the mixing further includes addition of a binding agent.

10. The method of claim 9, wherein the binding agent comprises a polymer, a saccharide, a polysaccharide, a carbohydrate, a fatty acid, an oil, an amino acid, or a combination thereof.

11. The method of claim 9, wherein the binding agent promotes adhesion between spores and/or vegetative cells and the aggregate particles via hydrophobic bonds, hydrophilic bonds, ionic bonds, non-ionic bonds, covalent bonds, van der Waal forces, or a combination thereof.

12. The method of claim 1, wherein the aggregate particles comprise natural, non- natural, recycled or manufactured sand, ore, rock, stone, minerals, crushed materials, fractured glass, mine tailings, paper, waste materials, plastics, polymers, roughened materials, and/or any combinations thereof.

13. The method of claim 1, wherein the aggregate particles are in the form of beads, grains, strands, fibers, flakes, crystals, or combinations thereof.

14. The method of claim 1, wherein the aggregate particles comprise particles with a mesh size of 100 or smaller.

15. The method of claim 14, wherein the mesh size is 200 or smaller.

16. The method of claim 1, wherein the concentration of the spores produced in (b) is from about $10^8$ to about $10^{10}$ spores/mL.

17. The method of claim 1, wherein the aqueous medium stimulates spore formation.

18. The method of claim 1, wherein the aqueous medium maintains viability of the spore-forming bacteria without propagation.

19. The method of claim 1, wherein (d) concentrates the spores or vegetative cells with the aggregate until the mixture contains less than 10% liquid by weight.

\* \* \* \* \*